Nov. 18, 1947. L. SCHULMAN Re. 22,935
CATAMENIAL BANDAGE MAKING MACHINE
Original Filed Feb. 18, 1939 6 Sheets-Sheet 1
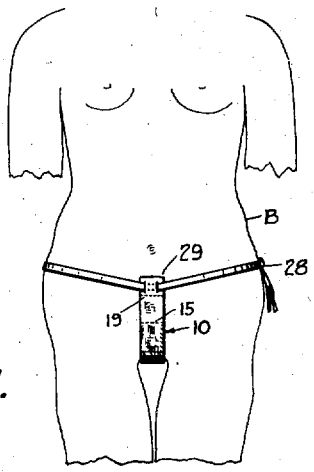
Fig. 1.
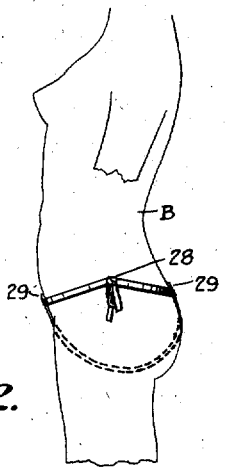
Fig. 2.
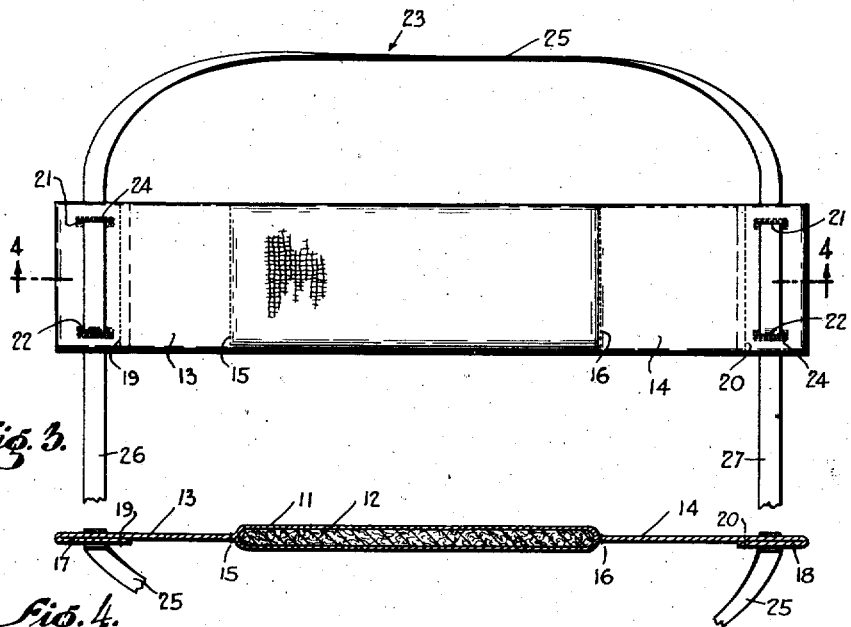
Fig. 3.
Fig. 4.
INVENTOR.
Louis Schulman.
BY Maxwell E. Sparrow
ATTORNEY.

Nov. 18, 1947. L. SCHULMAN Re. 22,935

CATAMENIAL BANDAGE MAKING MACHINE

Original Filed Feb. 18, 1939 6 Sheets-Sheet 2

INVENTOR.
Louis Schulman.
BY Maxwell E. Sparrow
ATTORNEY.

Nov. 18, 1947. L. SCHULMAN Re. 22,935

CATAMENIAL BANDAGE MAKING MACHINE

Original Filed Feb. 18, 1939 6 Sheets-Sheet 3

INVENTOR.
Louis Schulman.
BY
Maynard E. Sparrow
ATTORNEY.

Nov. 18, 1947. L. SCHULMAN Re. 22,935

CATAMENIAL BANDAGE MAKING MACHINE

Original Filed Feb. 18, 1939 6 Sheets-Sheet 4

INVENTOR.
Louis Schulman.

BY Maxwell E. Spanow
ATTORNEY.

Nov. 18, 1947. L. SCHULMAN Re. 22,935

CATAMENIAL BANDAGE MAKING MACHINE

Original Filed Feb. 18, 1939 6 Sheets-Sheet 5

INVENTOR.
Louis Schulman.
BY Maxwell E. Sparrow
ATTORNEY.

Nov. 18, 1947. L. SCHULMAN Re. 22,935

CATAMENIAL BANDAGE MAKING MACHINE

Original Filed Feb. 18, 1939 6 Sheets-Sheet 6

INVENTOR.
Louis Schulman.
BY Maxwell E. Sparrow
ATTORNEY.

Reissued Nov. 18, 1947 Re. 22,935

UNITED STATES PATENT OFFICE 22,935

CATAMENIAL BANDAGE MAKING MACHINE

Louis Schulman, deceased, late of Brooklyn, N. Y., by Stella Schulman, administratrix, New York, N. Y.; said Louis Schulman assignor of thirty-three and one-third per cent to Maxwell E. Sparrow, New York, N. Y., and said Stella Schulman, administratrix of said Louis Schulman, deceased, assignor of eleven and two-thirds per cent to Maxwell E. Sparrow, New York, N. Y.

Original No. 2,352,228, dated June 27, 1944, Serial No. 257,117, February 18, 1939. Application for reissue June 21, 1945, Serial No. 600,687

10 Claims. (Cl. 154—29)

1

This invention relates generally to improvements in bandages and their suspension means, particularly catamenial bandages; and more specifically to the making, folding and packaging of catamenial bandages. Reference is hereby made to my copending applications Serial Numbers 541,818 and 541,819, which are divisional applications hereof.

In a catamenial bandage or the so-called "sanitary napkin," the thickness is not uniform throughout its length. This non-uniformity in thickness is due to the practical requirement of having the substantially thick absorbent portion of the bandage at its intermediate area, and the thin tabs at its ends for suspension thereof and for the comfort of the wearer.

This non-uniformity in the thickness of a catamenial bandage presents a problem which must be considered in the production, folding and packing thereof, particularly, when it is desired to provide a catamenial package in compact form, enabling, for instance, a woman to conveniently carry the same in her handbag or to permit the same to be dispensed from a vending machine. In the production, folding and packaging of a catamenial bandage according to this invention, this problem is taken into consideration.

It is an object to present a package containing a catamenial bandage in compact form, by accordion-pleating or folding the bandage and compressing the same into a small individual package; thus enabling the package to be conveniently carried in a woman's handbag, or to be dispensed from a vending machine.

Further objects of the present invention reside in the provision of means for making catamenial bandages and also in the means for folding and compressing the same into small individual package.

It is a further object of the present invention to provide an improved and novel combined bandage and suspension means or support therefor, which is practical, efficient, economical and easily adjustable upon the wearer.

In addition to affording positive securing with respect to the supporting of the bandage, the present invention has the advantage of providing instrumentalities for keeping the ends of the bandage in a spread and flattened condition, the spreading effect operating very materially to reduce excessive bulkiness, rendering the connecting ends unusually flat and compact.

It is a further object of the present invention to produce a bandage with a supporting means

2 which will prevent the supported ends of the bandage from "gathering" or "puckering," and thus allowing the said ends to lie flat against the body of the wearer.

A further object of the present invention is to provide a catamenial device which will allow of proper adjustment upon the wearer, and which will avoid the use of common or conventional fasteners and supporters.

It is a further object of the present invention to provide a catamenial bandage which will remain flat against the body or garment of the user, and not mar the graceful lines of dresses, particularly tight-fitting ones, or destroy the effect of delicate sheer fabrics.

Still another object of the present invention is to provide a flat-lying catamenial bandage, which will not cause any discomfort to the wearer.

With the above and other objects in view, the invention comprises certain details of construction and arrangement of parts as will be hereinafter more fully described, illustrated and claimed, reference being had to the accompanying drawings which form a part of this specification and in which:

Fig. 1 is a front view of a sanitary belt and napkin or catamenial bandage embodying the invention, and shown as applied to a body;

Fig. 2 is a side view of Fig. 1;

Fig. 3 is a top plan view of a belt and napkin or bandage according to one embodiment of the invention;

Fig. 4 is a sectional view taken through line 4—4 of Fig. 3;

Figure 8:
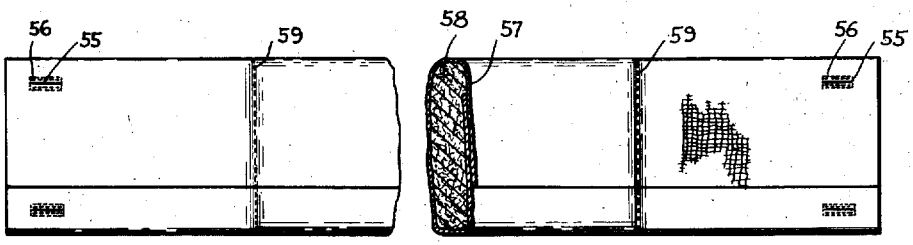
Fig. 8 is a top plan view (partly broken away) of the napkin shown in Fig. 7 in flattened condition.
Figure 8A:
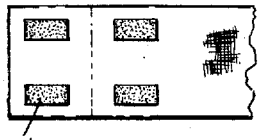
Figure 8B:
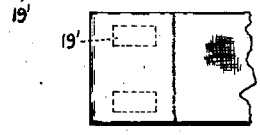
Figure 9:
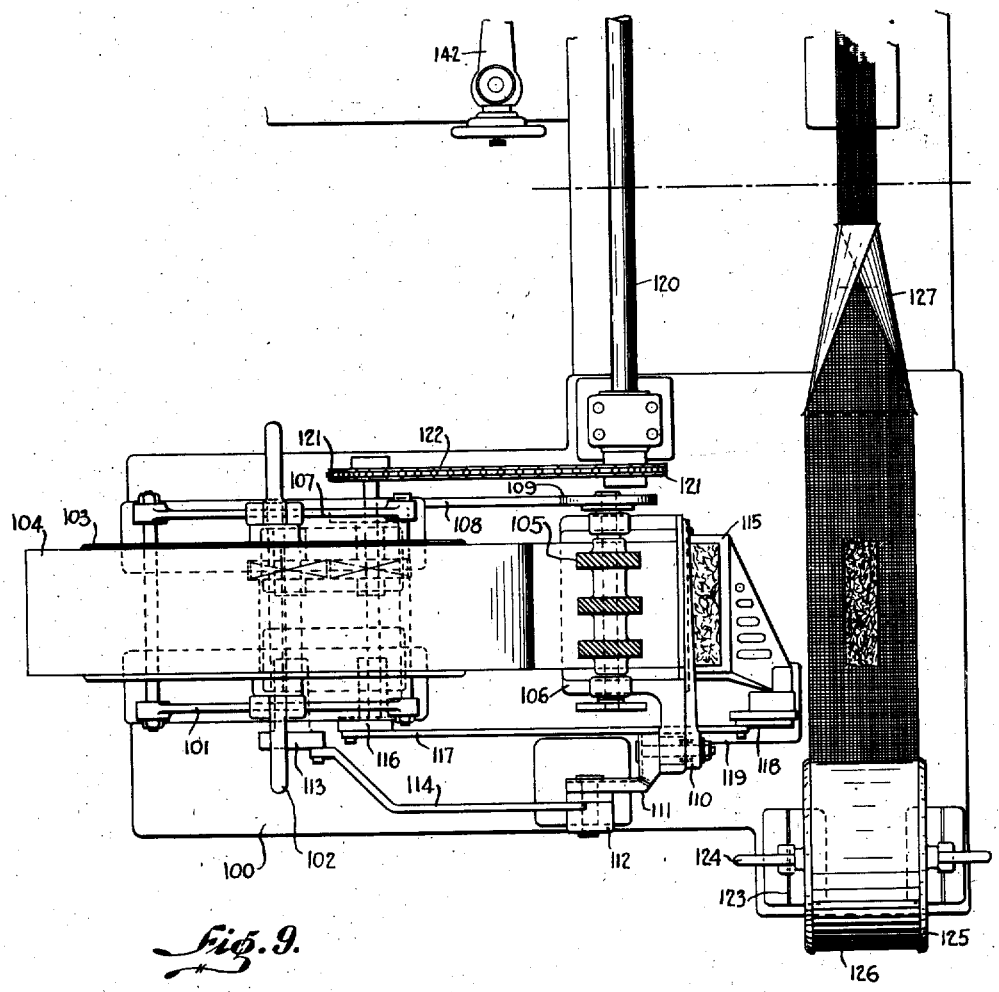
Figure 10:
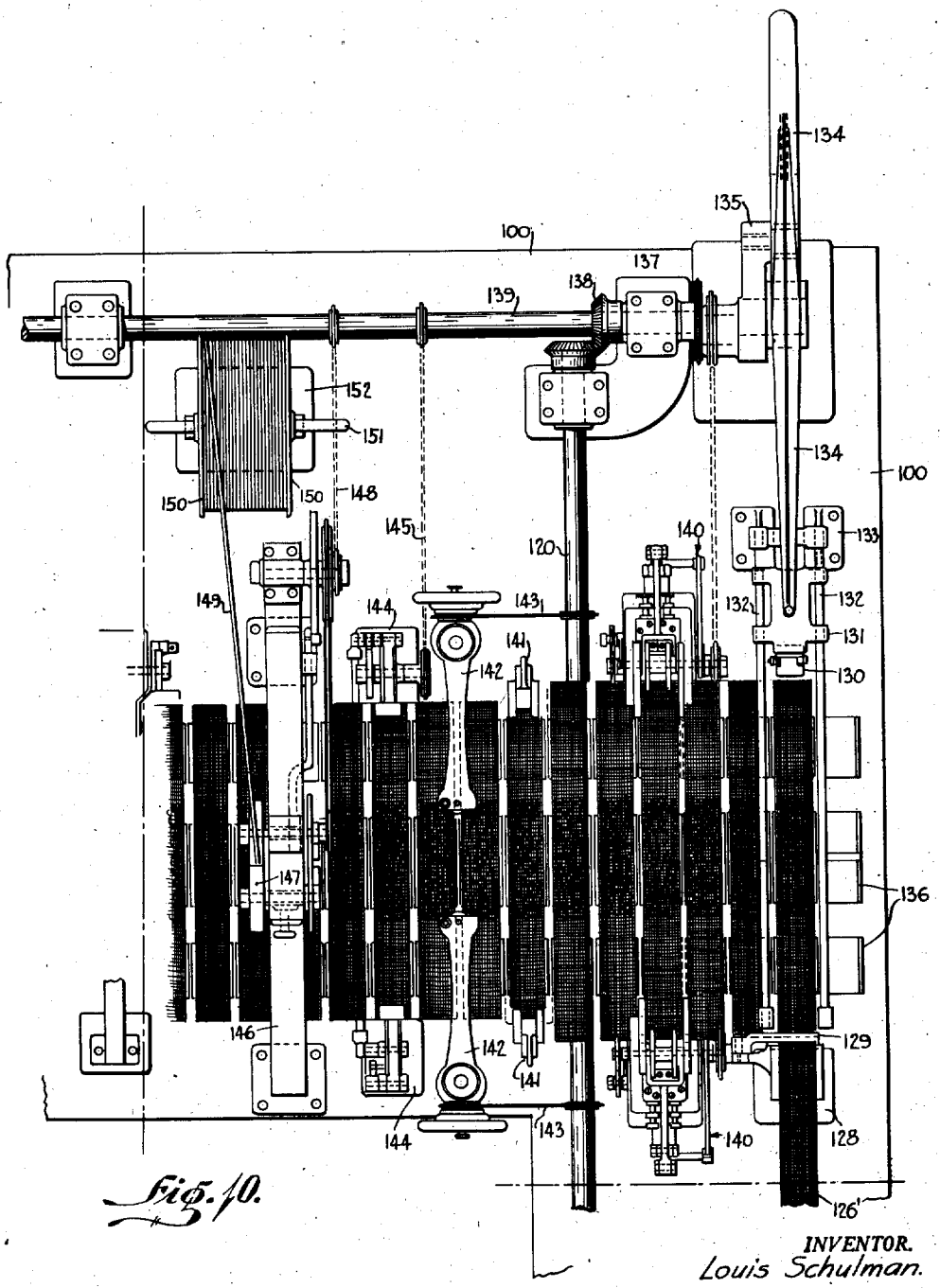
Figure 11:
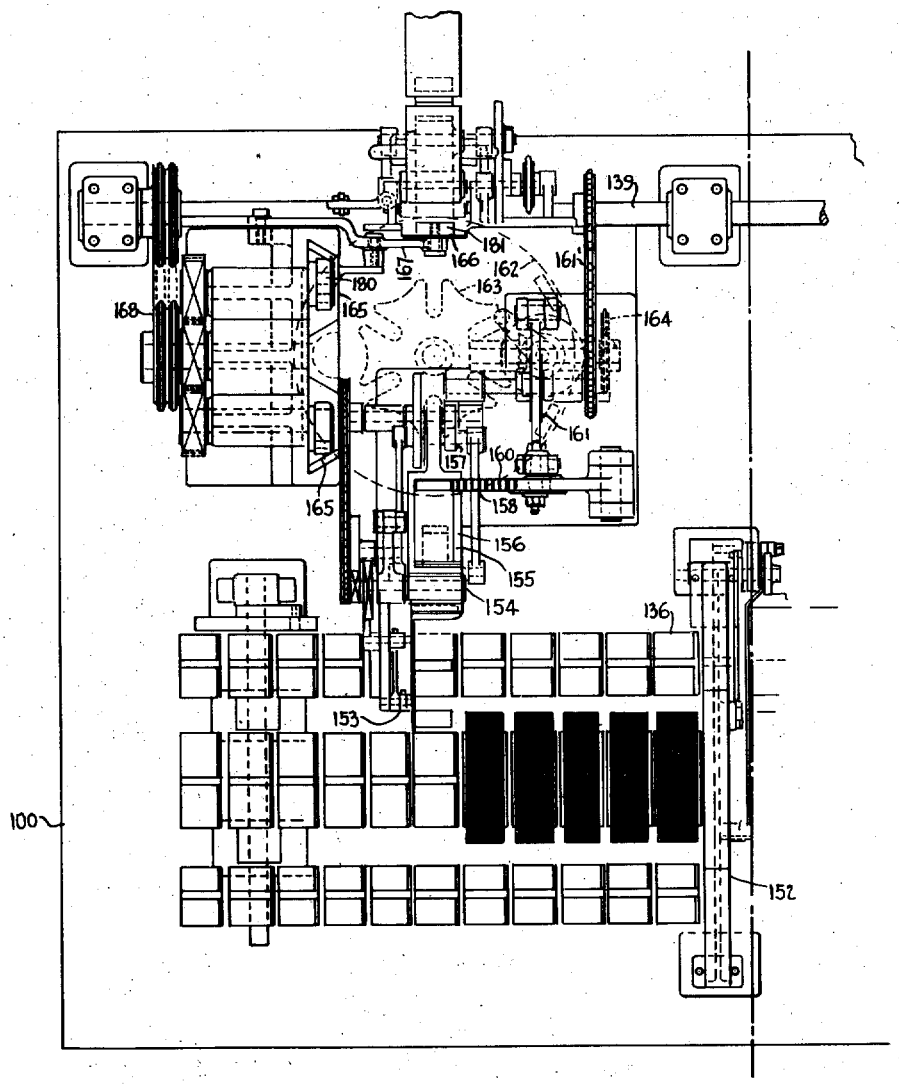
Figure 12:
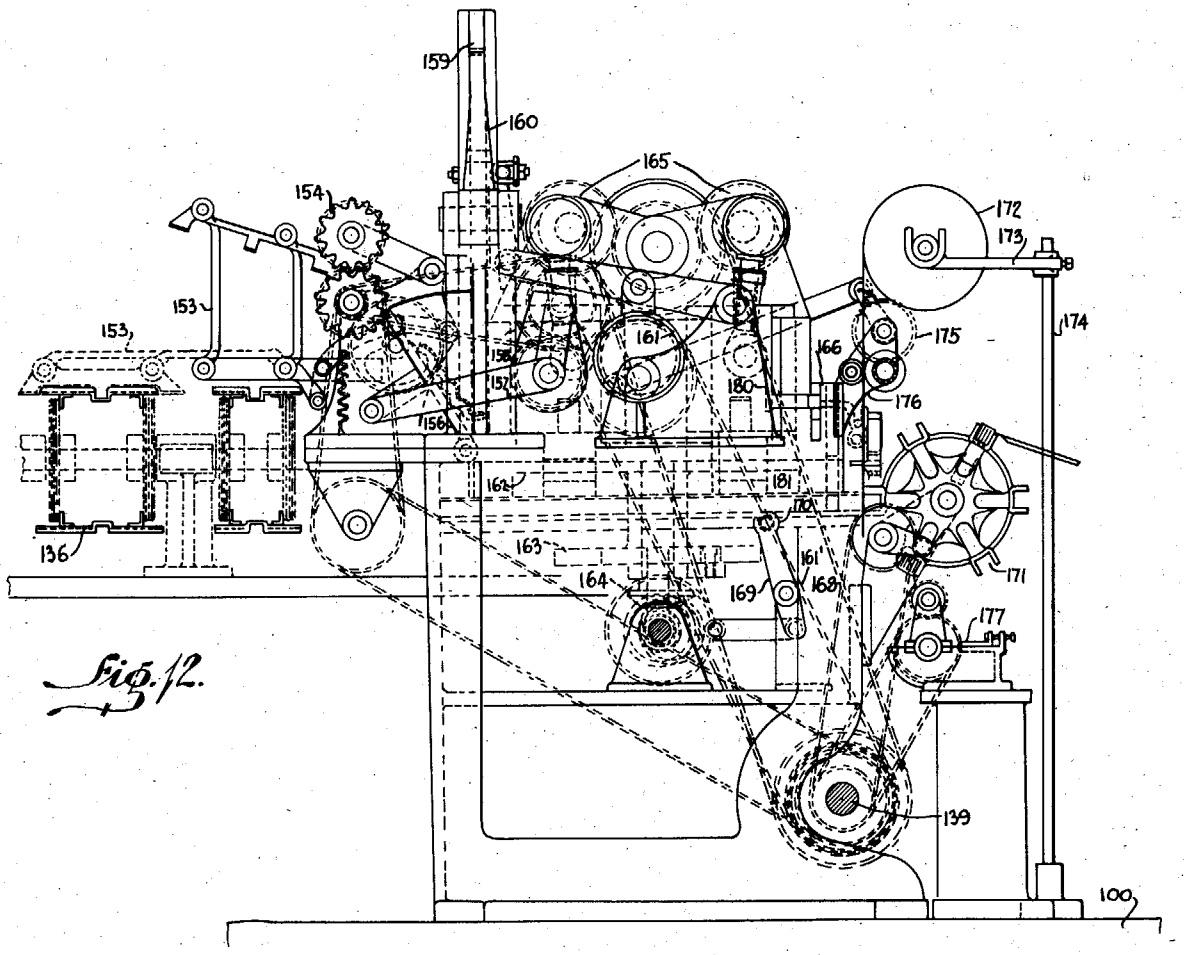

Figs. 8*a* and 8*b* are views of a portion of a catamenial bandage (adjacent the buttonholes) made in accordance with the invention;

Fig. 9 illustrates a plan view of the material feeding devices;

Fig. 10 illustrates a plan view of the conveyer system and the various mechanisms employed in the production of the sanitary napkin;

Fig. 11 is a plan view showing a construction of the conveyer system leading up to the final compression and wrapping of the sanitary napkin; and Fig. 12 is a side view (partly in section) of Fig. 11.

Referring to the drawings and particularly to Figs. 1–4 which show one example by which the invention may be realized, the numeral 10 indicates generally a catamenial bandage conventionally known as a sanitary napkin which may comprise a gauze shell 11 and a filler 12 of absorbent material which may be of the conventional type and which is located in the center portion of bandage or napkin 10, there being left the two free ends 13, 14. Shell 11 is formed by wrapping the gauze around the absorbent filler 12. The ends 13, 14 will, therefore, in this instance, consist of a plurality of layers of gauze. The filler 12 is held captive and prevented from shifting by the rows of stitches 15, 16. The free ends have folded-over portions 17, 18 which are secured to the body of the ends by means of lines of stitching 19, 20.

Each free end of the bandage 10 at its folded-over portion is provided with preferably two spaced-apart slots 21, 22 through which an end of the belt 23 is laced. These slots 21, 22 are preferably reinforced by stitches 24 and may be made in a conventional manner as by a buttonhole machine. Belt 23 is laced through the napkin 10 to provide a loop 25 on one side thereof, the belt ending on the other side of the napkin in two free ends 26, 27, which, when the napkin is adjusted on the wearer, are tied together into a conventional knot or bow 28 (Figs. 1 and 2). By lacing the belt 23 through the buttonholes 21, 22, the former will hold the ends of the napkin 10 flat against the body "B" of the wearer as indicated at 29 in Fig. 1. Belt 23 preferably comprises an inexpensive narrow tape made of any suitable material, discardable with the napkin.

The belt may be made of elastic or inelastic material. Instead of the belt being looped at one end as at 25, it may be provided with two free ends (not shown), similar to the ends 26, 27, so that, the tapes may be tied on either side of the body to hold the bandage in suspension; or the belt may be provided with two looped portions or ends similar to 25, this being preferable particularly where elastic tape is employed as the suspension means.

By the construction hereinabove described there is provided a catamenial bandage which will not "pucker" or gather at the ends nor bulge thereat, but will remain flat against the body of the wearer and which will not be made manifest through the clothing.

Although the example heretofore described refers to the use of the invention as a catamenial bandage, it is understood, however, that the same is applicable where bandages are generally employed, particularly where it is desired that the bandage be kept flat against the body to avoid discomfort and irritation.

Figure 5:
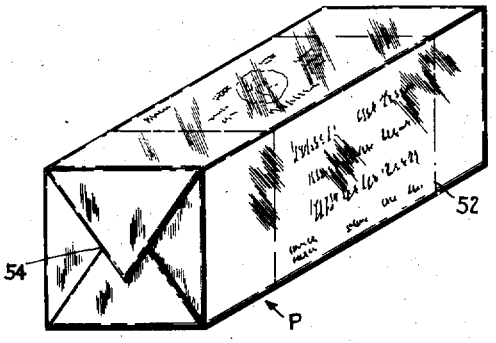
Fig. 5 is a perspective view of a package containing the catamenial bandage folded into accordion pleats.
Figure 6:
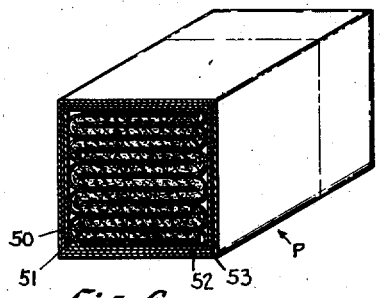
Fig. 6 is a cross-sectional view through the package illustrated in Fig. 5.
Figure 7:
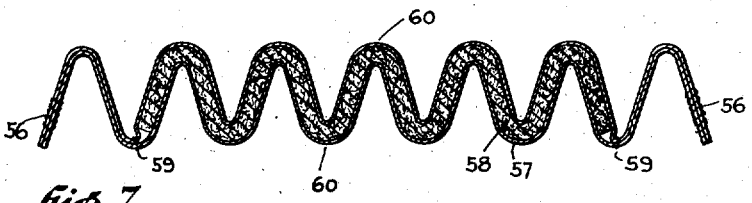
Fig. 7 is a sectional view through a napkin or bandage showing one typical way of folding the same.

A means of packaging the device is shown in Figs. 5–7. The package is preferably rectangular in shape, although it may be formed into any other shape. The package is made very compact by the means described later on so that it can be conveniently carried by the person or dispensed from a vending machine. For example, where the bandage is in the form of a catamenial bandage, both it and its supporting means may be arranged to provide a package of a size approximately 2⅝" long by ⅝" wide by ⅝" high, although the bandage is of conventional size.

In order to provide a very compact package the bandage may be transversely folded into accordion pleats or corrugatitons as clearly seen in Fig. 7. The accordion pleats 60 are preferably produced under pressure thereby reducing the dimensions of the bandage.

The package P seen in Fig. 5 contains the bandage or napkin 50 and the suspension or supporting tape or belt 23, in compressed accordion-pleated form. The bandage and support may be wrapped first in a covering 51 of tin foil over which is placed a label 52, the whole being then wrapped in a suitable, preferably transparent covering or wrapper 53, such as, "Cellophane" or other cellulose material. The tin foil wrapper 51 and the "Cellophane" cover 53 may be folded at the ends of the package as indicated at 54. In this embodiment in lieu of stitches 19, 20 there are provided the adhesive spots 19' (see Fig. 8*a*).

Fig. 8 shows a bandage 50 made in accordance with the invention, provided with the buttonholes 55 reinforced by the stitches 56. The bandage further has the gauze shell 57 and absorbent filler 58, which may be conventional, the filler being held in place by the stitches 59. The stitches 59 may be provided at the ends of the filler 58 as seen in Fig. 7, or they may pass through the ends of the filler.

A machine or mechanism which may be employed to produce the aforesaid catamenial bandage or sanitary napkin, preparing the same in pleated and compressed form for the wrapping operation, and initially wrapping the same will now be described. It will be evident that the following described machine may be employed to make and produce in compact form bandages, other than catamenial bandages.

Referring first generally to this machine, the absorbent material is contained on a spool of suitable diameter and is fed by a set of feed rolls operated intermittently through instrumentalities actuating a ratchet on said wheels. A predetermined portion of the absorbent material is fed to a knife properly spaced and the cut-off portion (12 of Figs. 3, 4 and 58 of Figs. 7, 8) is deposited on a transfer plate. This transfer plate makes a 180° movement and deposits the absorbent material in the center of the gauze.

The spool of gauze is located at right angles to the transfer plate so that the absorbent material is deposited on the gauze section proportionally to the length and width thereof.

The gauze having the section of absorbent material located thereon is then drawn through a folder which folds the gauze longitudinally into a flat tube of the proper size. The folded gauze is now drawn up to a knife by means of gripper jaws actuated by a segmental lever, which cuts the folded gauze to the proper length (indicated by the numeral 11 in Figs. 3, 4 and 57 in Figs. 7, 8). This cut length is deposited on a conveyer and is then brought to adhesive appliers which apply the adhesive (see 19' in Fig. 8*a*) on both ends of the cut gauze, simultaneously, by a system of segmental rolls which deposit the adhesive in predetermined spots. These adhesive spots are in lieu of the stitching 19, 20. From there the conveyer carries the same (cut folded gauze) to a set of folders which fold over the ends (17, 18 in Fig. 4) of the cut-folded gauze, approximately one inch from the ends and the same is then fed to a set of pressing rolls to adhesively secure the folded down ends. The conveyer then feeds the cut gauze to a set of sewing machines which sew transverse rows of stitches (15, 16, in Figs. 3, 4, and 59 of Figs. 7, 8) at each end of the absorbent material thereby preventing the absorbent material from shifting and securing the same in position within the folded gauze. The now formed bandage or napkin is brought by the conveyer to a set of perforating knives located on either end of said napkin and two or more buttonhole openings (21, 22 or 55) are perforated at each end of the napkin; after which the conveyer brings the napkin under a system of feed rolls which deposits a predetermined length of tape thereon, the latter being used as a means for securing the napkin to the body of the user. This tape 23 is fed from a spool by means of intermittent feed rolls which determine the proper length of tape desired and this length of tape is cut off. The conveyer then carries the napkin and the tape to a folder which folds the napkin transversely into three parts with the tape enclosed. The conveyer then carries the thus folded napkin with the enclosed tape to a lifting fork which deposits the napkin between a set of corrugated rolls. The corrugated rolls transversely corrugate, pleat, or crease the napkin and enclosed tape and the same is deposited on an inclined lifting platform which is a part of the mold wherein the napkin is first compressed. This platform is hinged at its lower end and when the napkin is deposited thereon by suitable means, this platform swings into a predetermined position between the side walls of the mold and the latter becomes a rectangular box. A plunger or ram descends within this box, initially compresses the folded and pleated napkin therein and presses it into a compartment or pocket of a dial plate located directly beneath the mold.

The dial plate then makes intermittent one-sixth turns, and brings the pocket or compartment containing the partially compressed napkin under plungers or rams for varying stages of compression. The reason for producing complete compression by stages is to gradually relieve the napkin of the confined air therein, and to thereby more compactly compress the napkin. The compression reduces the napkin to a smaller size than what is required, thus allowing for the expansion of the napkin which takes place upon release of the pressure produced by the plungers. Then the compressed pleated napkin with the suspension tape enclosed therein is brought under another plunger or ram which deposits the napkin on a transfer member below the dial plate. This transfer member is stationary. A ram or plunger operated by suitable means ejects it into a star wheel which is a part of the wrapping mechanism and is initially paper or foil wrapped. From this point on the compressed, pleated and paper-enfolded napkin may be further wrapped in any conventional manner.

Referring now to the drawings for a more detailed description, Fig. 9 shows a plan view of the material feeding devices for the sanitary napkin or catamenial bandage. The numeral 100 indicates a platform upon which is mounted a reel frame 101 carrying a mandrel 102. Mounted on mandrel 102 is a spool 103 carrying a roll of absorbent material 104. Mounted on frame work 106 by suitable brackets are the feed rolls 105 which are operated by a cam or eccentric 107 which in turn operates bar 108 actuating ratchet 109. Knife arm 110 is supported by bracket 106 mounted on platform 100. This knife severs the absorbent material after the proper amount has been fed, and is actuated by a pair of bevel segments 111 supported by bracket 112 mounted on platform 100. Crankplate 113 operates connecting rod 114 which in turn operates segments 111. Transfer plate 115 receives the cut absorbent material and by means of crankplate or cam 116 operating connecting rod 117 and segments 118, makes a 180° turn and transfers the absorbent material on the gauze in the proper location for subsequent operations. This transfer member is supported on bracket 119 and is mounted on platform 100. 120 is a power shaft and 121 is a pair of sprockets actuating chain 122 and supplying means to operate the aforementioned mechanism.

123 is a reel supporting a mandrel 124 and holds a spool 125 containing a roll of gauze 126 and mounted on platform 100. 127 indicates a folder in a fixed position; and by the simple act of drawing the gauze through the folder, the folder will cause a three-layer fold in the gauze. The folder 127 is mounted on platform 100.

As seen in Fig. 10, knife 129, mounted on bracket 128 severs the folded gauze to provide a napkin in desired length. Bracket 128 is mounted on platform 100.

A gripping member 130 is carried on sliding bracket 131 which slides on guide rods 132, the same being held by bracket 133 mounted on platform 100. The functioning of gripping member 130 is accomplished through the action of the arm 134 operated by crank 135 in the following manner. The arm 134 reciprocates through rotation of the crank 135; the jaws of gripping member 130 being held open by suitable means throughout the forward movement of arm 134. As the gripping member 130 passes underneath the upper knife 120, its jaws close on the folded gauze 126′ housing the absorbent material 104 enclosed therein.

On the return movement of the arm 134 the entire length of the napkin is drawn out, the gripper jaws of member 130 are opened, the end of the napkin is cut off by knife 129 and the napkin deposited on conveyer 136. An adhesive device 140 is arranged so as to be located at each end of the napkin. The rotary appliers 140 print the proper amount of adhesive (19′ Fig. 8a) on each end of the napkin and then return to their place of rest thereby releasing the napkin to be carried by the conveyer 136 for the next operation. Two rotary compression members 141 are hinged at their lower ends, and their function is to fold and press down the two ends of the napkin to make the adhesive stick. Two conventional sewing machines 142 are operated by shaft 120 through sprockets and chains 143. The napkin is brought by conveyer 136 to these machines which provide the stitches 15, 16 (Figs. 3, 4), 59 (Figs. 7, 8) confining the absorbent material in the gauze therebetween these stitches preventing shifting of the absorbent material during subsequent manipulations and also while the napkin is being worn.

Two perforating members 144, are provided which cut buttonholes or slits 55 (Fig. 8) through the adhesive cemented parts 19′ of the napkin as it is presented to these members 144, thus providing openings through which the tape 25 can be passed. This mechanism is operated by chain and sprockets 145 from the main shaft 139, all of which are mounted on platform 100.

A feeder 146 feeds a predetermined length of tape through the feed rolls 147 operated intermittently, and the said length of tape is then cut off by a knife (not shown). Feeder 146 is mounted on platform 100 and is operated through chain and sprockets 148 and power shaft 139.

Tape 149 is taken from spool 150 which is placed on mandrel 151 supported on reel 152 and mounted on platform 100.

As seen in Figs. 11 and 12, conveyer 136 carries the napkin to folder 152 (Fig. 11), which folds the napkin in three parts transversely and encloses the tape therein. Folder 152 is operated through chain and sprockets (not shown) and is driven by power shaft 139 and mounted on platform 100. Conveyer 136 carries the folded napkin with the tape enclosed therein to a forked lifting platform 153, the function of which is to lift the folded napkin from the conveyer 136 and bring the front end of the napkin to a position between a pair of pleating, indenting or creasing rolls 154, the latter rotating at a fairly rapid rate of speed, corrugating and then ejecting the napkin upon inclined plate 155 which is movable between side walls 156 of mold 156*a*. Plate 155 is hinged at the bottom of the mold 156*a* and together with side walls 156 form part of the mold wherein the napkin is compressed. After the deposit of the pleated napkin upon inclined plate 155, the latter is caused to swing to a closed position by action of cam and lever 157, 158 and converts mold 156*a* into a closed rectangular box. The ram 159 (shown in Fig. 12) descends within the mold box 156*a* and initially compresses the napkin.

The compression ram 159 is actuated by segment 160 and powered by a device 161 comprising levers, connecting links, and eccentric, the device being driven by chain and sprockets 161′ and power shaft 149. The result of the action of compression ram 159 on the corrugated napkin is to initially compress the same in box 156*a* and within a pocket 162*a* of the dial plate 162 as the said pocket 162*a* comes adjacent box or mold 156*a*. The dial plate has six pockets 162*a* which successively receive napkins from mold or box 156*a* and acts as a carrier for the napkins in their step by step stages or operations of compression. Dial plate 162 is actuated intermittently by the Geneva movement 163 driven by sprocket and chain 164 and power shaft 139.

The dial plate 162 rotating in clockwise direction brings each napkin being compressed respectively under the rams 180 of the duplex press 165 which progressively compress the napkin, ultimately into a compact body or mass, and making the same ready for ejection by the mechanism 166 which is the fourth and last stage in the compression system. The mechanism 166 comprises the ejecting ram operated by lever 167 pivoted on a ram 180 of duplex press 165 and actuated by the same. The duplex press 185 is driven by chain and sprockets 168 and powered by shaft 149. The completely compressed napkin in compact form is ejected into a receptacle located underneath the fourth pocket indicated by the numeral 181 of the dial plate 162 and is then further ejected into a star wheel 171 of the wrapping machine as shown in Fig. 12, all of the foregoing being mounted on platform 100.

Fig. 12 is a side view of Fig. 11 showing details not seen on Fig. 11. 169 is the lever actuating the ram 170 which ejects the compressed napkin into one of the pockets of the star wheel 171. 172 is a roll of wrapping material held in a bracket 173 and supported by stand 174 mounted on platform 100. 175 is a system of feed rolls held by bracket 176. 177 is an adhesive box which gums the end of the wrapping material. From this point on the wrapped bandage with its suspension means enclosed therein, may be further packaged as desired and in any suitable manner.

It can be readily understood that the invention is applicable to bandages in general and to various other forms of catamenial bandages.

Since the invention may be embodied in other specific forms without departing from the spirit or essential attributes thereof, it is, therefore, desired that the present embodiments be considered in all respects as illustrative and not restrictive; reference being had to the appended claims rather than to the foregoing description to indicate the scope of the invention.

Having described the invention, what is claimed as new and desired to be secured by Letters Patent is:

1. In a catamenial bandage making machine wherein absorbent material is fed, cut and deposited on gauze material and the gauze material folded over the cut absorbent material, the combination of means for gripping the folded gauze, means for moving the gripping means to draw the folded gauze a predetermined distance for a cutting operation, means for cutting a predetermined length of said folded gauze for producing a catamenial bandage, means for depositing adhesive on said bandage adjacent the ends thereof, means for folding over the ends of said bandage upon itself, means for pressing down said folded ends with the adhesive therebetween to form reinforced ends, means for perforating said bandage through said reinforced ends, means for depositing a predetermined length of tape upon said bandage, and means for folding end portions of said bandage transversely over its intermediate portion and said tape.

2. In a catamenial bandage making machine wherein absorbent material is fed, cut and deposited on gauze material and the gauze material folded over the cut absorbent material, the combination of means for gripping the folded gauze, means for moving the gripping means to draw the folded gauze a predetermined distance for a cutting operation, means for cutting a predetermined length of said folded gauze for producing a catamenial bandage, means for folding over the ends of said bandage upon itself, means for securing said ends in said folded over position to form reinforced ends for said bandage, means for perforating said bandage through said reinforced ends, means for depositing a predetermined length of tape upon said bandage, and means for folding end portions of said bandage transversely over its intermediate portion and said tape.

3. In a catamenial bandage making machine wherein absorbent material is fed, cut and deposited on gauze material and the gauze material folded over the cut absorbent material, the combination of means for cutting a predetermined length of said folded gauze for producing a catamenial bandage, means for folding over the ends of said bandage upon itself, means for securing said ends in said folded over position to form reinforced ends for said bandage, means for perforating said bandage through said reinforced ends, means for feeding tape, means for cutting a predetermined length of said tape, means for depositing said predetermined length of tape upon said bandage, and means for folding end portions of said bandage transversely over its intermediate portion and said tape.

4. In a catamenial bandage making machine wherein absorbent material is fed, cut and deposited on gauze material and the gauze material folded over the cut absorbent material, the combination of means for cutting a predetermined length of said folded gauze for producing a catamenial bandage, means for producing reinforced ends on said bandage, means for perforating said bandage through said reinforced ends, means for feeding tape, means for cutting a predetermined length of said tape, means for depositing said predetermined length of tape upon said bandage, and means for folding end portions of said bandage transversely over its intermediate portion and said tape.

5. In a catamenial bandage making machine wherein absorbent material is fed, cut and deposited on gauze material and the gauze material folded over the cut absorbent material, the combination of means for cutting a predetermined length of said folded gauze for producing a catamenial bandage, means for feeding tape, means for cutting a predetermined length of said tape, means for depositing said predetermined length of tape upon said bandage, and means for folding end portions of said bandage transversely over its intermediate portion and said tape.

6. In a catamenial bandage making machine wherein absorbent material is fed, cut and deposited on gauze material and the gauze material folded over the cut absorbent material, the combination of means for cutting a predetermined length of said folded gauze for producing a catamenial bandage, means for producing reinforced ends on said bandage, means for feeding tape, means for cutting a predetermined length of said tape, means for depositing said predetermined length of tape upon said bandage, and means for folding end portions of said bandage transversely over its intermediate portion and said tape.

7. In a catamenial bandage making machine wherein absorbent material is fed, cut and deposited on gauze material and the gauze material folded over the cut absorbent material, the combination of means for gripping the folded gauze, means for moving said gripping means to draw the folded gauze a predetermined distance for a cutting operation, means for cutting a predetermined length of said folded gauze for producing a catamenial bandage, means for feeding tape, means for cutting a predetermined length of said tape, means for depositing said predetermined length of tape upon said bandage, and means for folding end portions of said bandage transversely over its intermediate portion and said tape.

8. A bandage making machine comprising means for feeding absorbent material, means for feeding gauze or the like, means for depositing said material on said gauze and including a transfer member, means for folding said gauze longitudinally over said material into a substantially flat tube for forming a bandage, means for depositing a predetermined length of tape upon said bandage, and means for folding said bandage over said tape.

9. A bandage-making machine comprising means for feeding absorbent material, means for feeding gauze or the like, means for depositing said material on said gauze, means for folding said gauze longitudinally over said material into a substantially flat tube for forming a bandage, means for depositing a predetermined length of tape upon said bandage, and means for folding said bandage over said tape.

10. A bandage-making machine comprising means for feeding absorbent material, means for feeding gauze or the like, means for depositing said material on said gauze, means for folding said gauze longitudinally over said material into a substantially flat tube for forming a bandage, means for securing the folds of said gauze adjacent the ends of said material to prevent endwise shifting of said material, means for depositing a predetermined length of tape upon said bandage, and means for folding said bandage over said tape.

STELLA SCHULMAN.
*Administratrix of the Estate of Louis Schulman, Deceased.*

REFERENCES CITED

The following references are of record in the file of this patent:

UNITED STATES PATENTS

| Number | Name | Date |
|---|---|---|
| 1,022,894 | Sprague | Apr. 9, 1912 |
| 1,048,779 | Woodhead | Dec. 31, 1912 |
| 1,794,358 | Bauer | Mar. 3, 1931 |
| 1,825,492 | Wandel | Sept. 29, 1931 |
| 1,845,436 | O'Neill | Feb. 16, 1932 |
| 1,957,651 | Joa | May 8, 1934 |
| 1,973,737 | Williams | Sept. 18, 1934 |
| 2,039,425 | Jurgensen | May 5, 1936 |

FOREIGN PATENTS

| Number | Country | Date |
|---|---|---|
| 488,469 | Germany | Dec. 28, 1929 |